(12) United States Patent
Lu et al.

(10) Patent No.: US 8,535,574 B2
(45) Date of Patent: Sep. 17, 2013

(54) TRANSITION METAL COMPLEXES, MANUFACTURING METHOD THEREOF, PHOTOVOLTAIC CELLS AND MANUFACTURING METHOD THEREOF

(75) Inventors: Norman Lu, Banqiao (TW); Jia-Sheng Shing, Yongjing Township (TW); Wen-Han Tu, Yingge Township (TW)

(73) Assignee: National Taipei University of Technology (TW)

( * ) Notice: Subject to any disclaimer, the term of this patent is extended or adjusted under 35 U.S.C. 154(b) by 534 days.

(21) Appl. No.: 12/760,664

(22) Filed: Apr. 15, 2010

(65) Prior Publication Data

US 2011/0253216 A1    Oct. 20, 2011

(51) Int. Cl.
H01B 1/22    (2006.01)
H01L 31/0256    (2006.01)

(52) U.S. Cl.
USPC ... 252/519.2; 252/514; 252/513; 252/519.13; 252/519.21; 252/519.14; 252/519.4; 252/520.3; 252/521.2; 136/261; 136/263; 546/12

(58) Field of Classification Search
USPC .......... 252/514, 513, 519.13, 519.21, 519.2, 252/519.14, 519.4, 520.3, 521.2; 136/261, 136/263; 546/12
See application file for complete search history.

(56) References Cited

U.S. PATENT DOCUMENTS

| | | | |
|---|---|---|---|
| 5,463,057 A * | 10/1995 | Graetzel et al. | 546/4 |
| 5,789,592 A * | 8/1998 | Gratzel et al. | 546/21 |
| 7,932,404 B2 * | 4/2011 | Zakeeruddin et al. | 549/50 |
| 2007/0017569 A1 * | 1/2007 | Gui et al. | 136/256 |
| 2007/0039644 A1 * | 2/2007 | Lee et al. | 136/252 |
| 2009/0000658 A1 * | 1/2009 | Zakeeruddin et al. | 136/252 |
| 2009/0111957 A1 * | 4/2009 | Lu et al. | 526/172 |
| 2011/0265876 A1 * | 11/2011 | Zakeeruddin et al. | 136/263 |
| 2012/0184748 A1 * | 7/2012 | Lu et al. | 546/271.1 |

OTHER PUBLICATIONS

Norman Lu et al., "The intramolecular blue-shifting C—H . . . F—C hydrogen bond", CrystEngComm, 2010, 12, 538-542 (first published Sep. 30, 2009).*
Norman Lu et al., "4,4'-Bis(2,2,2-trifluoroethoxymethyl)-2,2'-bipyridine", Acta Cryst. (2010), C66, o289-o291.*
Norman Lu et al., "Novel Fluorous Amphiphilic Heteroleptic Ru-Based Complexes for Dye-Sensitized Solar Cell", Inorg. Chem., 2011, 50, 4289-4294.*
Peng Wang et al., "A stable quasi-solid-state dye-sensitized solar cell with an amphiphilic ruthenium sensitizer and polymer gel electrolyte", Nature Materials, Jun. 2, 2003, 402-408.*
Lu et al.; "New bis(fluoro-ponytailed) bipyridine ligands for Pd-catalyzed Heck reactions under fluorous biphasic catalysis condition"; ScienceDirect, Tetrahedron 63 (2007) 2019-2023.
Lu et al.; "Efficient, recoverable, copper-catalyzed aerobic oxidation of alcohols under FBS and thermomorphic mode"; ScienceDirect, Tetrahedron Letters 48 (2007) 8823-8828.
Lu et al.; (2,2'-Bipyridine)palladiumdichloride Derivatives as Recyclable Catalyssts in Heck Reactions; Journal of the Chinese Chemical Society, 2006, 53, 1517-1521.
Lu et al.; Synthesis, structure and reactivity of novel palladiumdichloride-2,2'-bipyridine with 4,4'-bis(fluorous-ponytail); ScienceDirect, Polyhedron 26 (2007) 3045-3053.

* cited by examiner

*Primary Examiner* — Douglas McGinty
(74) *Attorney, Agent, or Firm* — Schmeiser, Olsen & Watts LLP (57) ABSTRACT

This invention provides a transition metal complex of formula $MXY_2Z$ and a manufacturing method thereof, wherein M is selected from iron, ruthenium, and osmium; X represents a ligand shown in formula (II)

(II)

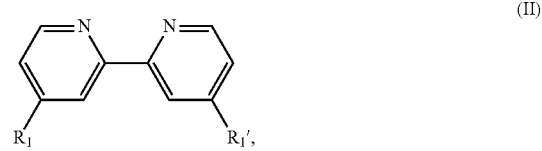

wherein $R_1$ and $R_1'$ are independently selected from COOH, $PO_3H_2$, $PO_4H_2$, $SO_3H_2$, $SO_4H_2$, and derivatives thereof; Y is selected from $H_2O$, Cl, Br, CN, NCO, NCS, and NCSe; Z represents a bidentate ligand having at least two fluorinated chains. In addition, this invention also provides photovoltaic cells and a manufacturing method thereof.

1 Claim, 3 Drawing Sheets

TRANSITION METAL COMPLEXES, MANUFACTURING METHOD THEREOF, PHOTOVOLTAIC CELLS AND MANUFACTURING METHOD THEREOF

FIELD OF THE INVENTION

This invention relates to transition metal complexes and more particularly to transition metal complexes used in the preparation of dye-sensitized solar cells (DSSCs).

BACKGROUND OF THE INVENTION

Sensitizers are one of the most crucial components for the preparation of DSSCs because they affect not only the incident photon conversion efficiency (IPCE) of the cells but also the stability of the components.

Thus far, various sensitizers have been proposed by scientists in hopes of increasing the efficiency of DSSCs and prolonging their service life. For example, Michael Grätzel, a Swiss scientist, developed in 1999 a sensitizer named N719, which was widely used in the industry for its high IPCE.

However, because N719 cannot sustain high temperature and falls off easily after being used for a period of time, solar cells containing the same usually can no longer work normally after three years of usage.

In order to improve the stability of N719 under the existence of a heat source or in a moist condition, Grätzel further proposed in 2003 another sensitizer named Z907. Proved by experiments, Z907 can still possess 94% of its original efficiency after being operated continuously for 1,000 hours under 80° C. In contrast, the efficiency of N719 decreases 35% under the same condition.

Although Z907 demonstrates great sustainability in long-term stability testing, Z907 is not completely satisfactory because it has a molar absorption coefficient lower than N719.

Accordingly, it is highly desirable for scientists to develop novel sensitizers with high IPCE and thermal stability.

SUMMARY OF THE INVENTION

In view of the demands for developing a new generation of sensitizers in the industry, one of the objectives of this invention is to provide novel transition metal complexes and manufacturing methods thereof, wherein the transition metal complexes are applicable to the preparation of photovoltaic cells.

It is another objective of this invention to provide a transition metal complex having a general formula $MXY_2Z$, wherein M is selected from iron, ruthenium, and osmium; X is a ligand shown by formula (II):

wherein $R_1$ and $R_1'$ are independently selected from COOH, $PO_3H_2$, $PO_4H_2$, $SO_3H_2$, $SO_4H_2$ and derivatives thereof; Y is selected from $H_2O$, Cl, Br, CN, NCO, NCS and NCSe; and Z is a bidentate ligand with two or more fluorinated chains.

Preferably, M is ruthenium; $R_1$ and $R_1'$ are independently selected from COOH, $PO_3H_2$, and derivatives thereof; Y is NCS; Z is bipyridine with at least two fluorinated chains which are located on different pyridyl rings.

Preferably, bipyridine is substituted by a fluorinated functional group having a spacer, which is preferably an ether linkage or at least one methylene structure. In addition, Z preferably comprises at least one fluorinated chain of formula (IV):

wherein m and n are each independently an integer greater than zero, such as 1, 2 or 3, and $R_f$ is a fluorinated alkyl chain, such as $-CF_2-CF_2H$, $-CF_2-CF_2-CF_3$, $-CF_2-CF_2-CF_2-CF_2H$, etc.

Preferably, the fluorinated chains of Z are independently substituted by 1 to 30 fluorine atoms and more preferably by 1 to 20 fluorine atoms. Most preferably, the fluorinated chains of Z are independently substituted by 4, 7, 8, 12, 13 or 19 fluorine atoms.

It is another objective of this invention to provide a transition metal complex having the following chemical structure:

wherein $FC_1$ and $FC_2$ are each independently a fluorinated chain with a spacer.

Preferably, $FC_1$ and $FC_2$ can be substituted at position number 4 or 5 of the pyridyl ring, and $FC_1$ or $FC_2$ can be fluorinated functional group having a spacer, such as $-CH_2-O-CH_2-R_f$, wherein $R_f$ is a linear or branched fluorinated alkyl chain, such as an alkyl chain containing 4, 7, 8, 12, 13 or 19 fluorine atoms.

It is another objective of this invention to provide a method of preparing the above-mentioned transition metal complexes, wherein the improvement comprises using a chelating agent of the following formula:

wherein $R_f$ is an alkyl chain substituted by 1 to 30 fluorine atoms.

It is still another objective of this invention to provide a method of preparing photovoltaic cells, the method comprising:

providing a transition metal complex having a general formula $MXY_2Z$, wherein M is selected from iron, ruthenium, and osmium; X is a ligand shown by formula (II):

(II)

wherein $R_1$ and $R_1'$ are independently selected from COOH, $PO_3H_2$, $PO_4H_2$, $SO_3H_2$, $SO_4H_2$ and derivatives thereof; Y is selected from $H_2O$, Cl, Br, CN, NCO, NCS and NCSe; and Z is a bidentate ligand with two or more fluorinated chains; and preparing photovoltaic cells by using the transition metal complex.

It is yet another objective of this invention to provide a photovoltaic cell, which comprises an anode having a conductive substrate and a metal-oxide-semiconductor layer formed on the conductive substrate, the metal-oxide-semiconductor layer being treated by a sensitizing dye; a counter electrode; and an electrolyte provided between the counter electrode and the metal-oxide-semiconductor layer, wherein the sensitizing dye is a bidentate ligand with at least two fluorinated chains.

It is yet another objective of this invention to provide a transition metal complex and a method of manufacturing the same. The transition metal complex has unexpectedly high IPCE and desirable thermal stability and thereby is applicable to the production of photovoltaic cells with great quality.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Example 1

Preparation of Transition Metal Complexes

Figure 1:
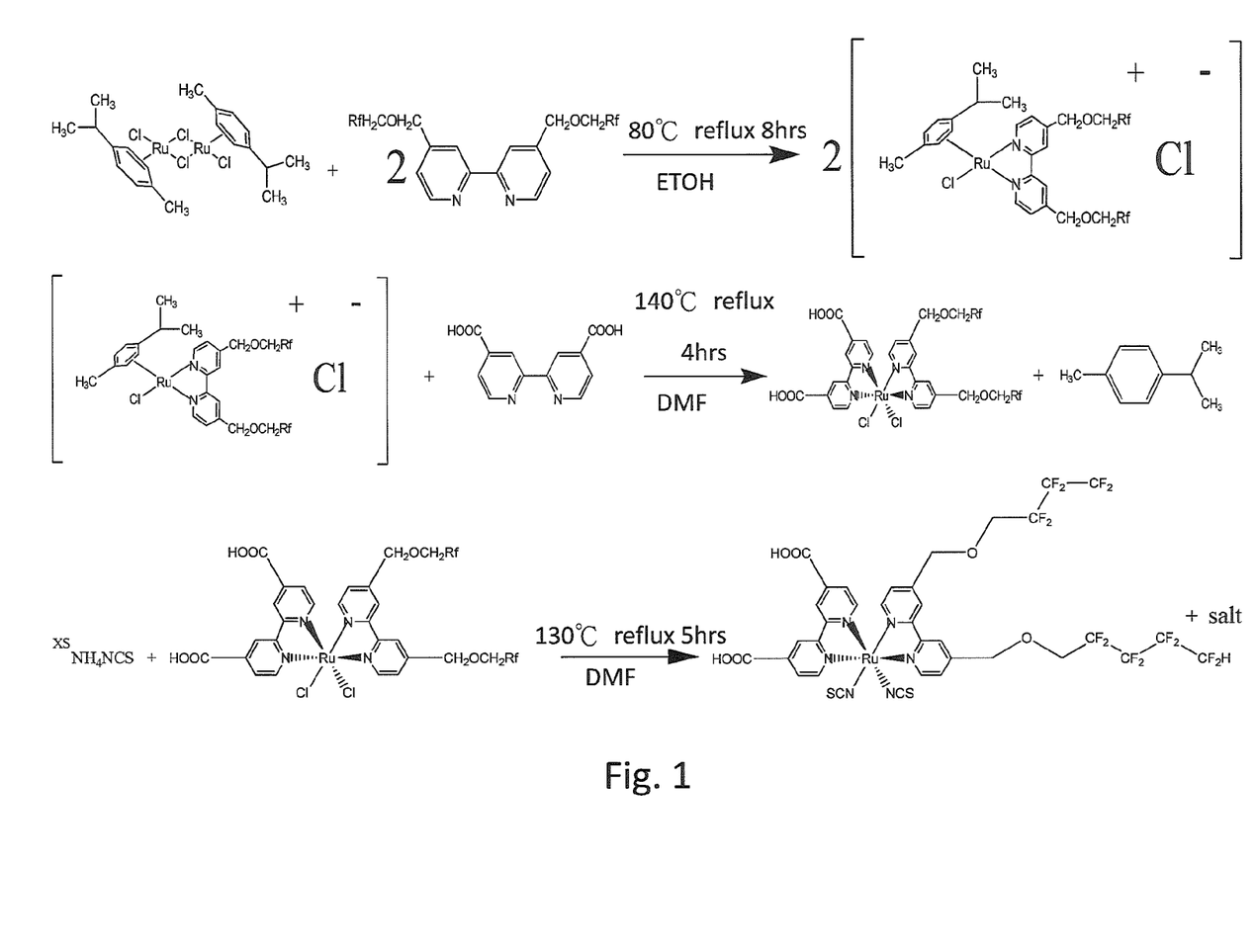
FIG. 1 shows the main steps for preparing a transition metal complex of this invention.

FIG. 1 shows the main steps for preparing a transition metal complex of this invention, from which it can be observed that bipyridine containing —$(CH_2)_m$—O—$(CH_2)_n$—$R_f$ is used to chelate the transition metal. Details for the preparation of the chelating agent can be found at N. Lu, J-Y Chen, C-W Fan, Y-C Lin, Y-S Wen, L-K Liu, *J. Chin. Chem. Soc*, 2006, 53, 1517-1521; N. Lu, Y-C Lin, J-Y Chen, C-W Fan, L-K Liu, *Tetrahedron*, 2007, 63, 2019-2023; N. Lu, Y-C Lin, J-Y Chen, T-C Chen, S-C Chen, Y-S Wen, L-K Liu, *Polyhedron*. 2007, 26, 3045-3053; and N. Lu, Y-C Lin, *Tetrahedron Lett*. 2007, 48, 8823-8828, all of which are incorporated by reference herein. In the above-mentioned formula, m and n are each independently an integer greater than zero, and when $R_f$ is —$CF_2$—$CF_2H$, —$CF_2$—$CF_2$—$CF_3$, and —$CF_2$—$CF_2$—$CF_2$—$CF_2H$, the transition metal complexes produced thereby are named CT4, CT7 and CT8, respectively.

1-1: Preparation of CT8

Dichloro(p-cymene)-ruthenium(II) dimer (Aldrich, 0.38 g, 0.62 mmol) and bipyridine having substitution of eight fluorine atoms at each ring (0.8 g, 1.24 mmol) were dissolved in 60 ml ethanol and then the solution was stirred and refluxed for 8 hours at 80° C. under $N_2$ atmosphere. After pumping away ethanol, Bpy-COOH (0.30 g, 1.24 mmol) and 40 mL dry DMF were added. The reaction mixture was refluxed at 140° C. for another 4 hours at dark. Excess $NH_4NCS$ (SHOWA, 2.92 g, 38.44 mmol) was added to the reaction mixture and heated at 130° C. for 5 hours. After reaction, the solvent was removed with a rotary vacuum pump and large amount of water was added to dissolve the excess $NH_4NCS$. Then 1.18 g (1.06 mmol) dark purplish red solid product CT8 was obtained after vacuum filtration.

In order to obtain purer dye, the solid product was treated with TBAOH (tetrabutylammonium hydroxide), and the resulting TBA salt was dissolved in methanol then passed through the chromatography column (Sephadex LH20) using methanol as an eluent. The main band was collected and concentrated, and the solvent was extracted by an evaporator. The process was repeated five times; then some water was added, and 0.02 M $HNO_3$ was added to adjust the pH value to precipitate the product. The product was placed in a refrigerator for 24 hours, followed by vacuum filtration at room temperature to obtain CT8-TBA.

1-2 Identification Data of CT8 and CT8-TBA

Identification Data of CT8

$^1$H-NMR (500 MHz, $CD_3OD$), δ (ppm):

9.61 (d, $H_6$, $^3J_{HH}$=5.5 Hz); 9.36 (d, $H_6'$, $^3J_{HH}$=5.5 Hz); 9.01 (s, $H_3$); 8.86 (s, $H_3'$); 8.49 (s, $H_3'''$); 8.34 (s, $H_3''$); 8.21 (d, $H_6'''$, $^3J_{HH}$=6.4 Hz); 7.84 (d, $H_5$, $^3J_{HH}$=5.5 Hz); 7.79 (d, $H_6''$, $^3J_{HH}$=4.6 Hz); 7.60 (d, $H_5'$, $^3J_{HH}$=5.5 Hz 7.52 (d, $H_5'''$, $^3J_{HH}$=6.4 Hz); 7.15 (d, $H_5''$, $^3J_{HH}$=4.6 Hz); 6.59 (tt, $H_{10}'''$, $^2J_{HF}$=50.8 Hz, $J^3{}_{HF}$=5.5 Hz, 2H); 6.50 (tt, $H_{10}''$, $^2J_{HF}$=50.8 Hz, $^3J_{HF}$=5.5 Hz, 2H); 5.06 (s, $H_8'''$, 2H); 4.79 (s, $H_8''$, 2H); 4.37 (t, $H_9'''$, $^3J_{HF}$=14 Hz, 2H); 4.17 (t, $H_9''$, $^3J_{HF}$=14 Hz, 2H)

$^{13}$C-NMR (113 MHz, $CD_3OD$), δ (ppm):

166.9 ($C_7$); 166.6 ($C_7'$); 160.9 ($C_2$); 159.7 ($C_2'$); 159.6 ($C_2''$); 158.3 ($C_2'''$); 155.1 ($C_6$); 154.0 ($C_6'$); 153.8 ($C_6''$); 152.9 ($C_6'''$); 149.9 ($C_4$); 149.2 ($C_4'$); 139.9 ($C_4''$); 139.3 ($C_4'''$); 127.0 ($C_3$); 126.3 ($C_3'$); 125.8 ($C_3''$); 125.1 ($C_3'''$); 123.7 ($C_5$); 123.6 ($C_5''$); 122.0 ($C_5''$); 122.0 ($C_5'''$); 135.3 ($C_{14}$ of NCS); 134.5 ($C_{14}'$ of NCS); 106-118 ($C_{10}'''$~$C_{13}'''$ and $C_{10}''$~$C_{13}'''$); 73.2 ($C_8'''$); 72.8 ($C_8''$); 69.0 ($C_8''$); 68.7 ($C_9''$)

$^{19}$F-NMR (470.5 MHz, $CD_3OD$), δ (ppm):

−121.3 (t, —$CH_2CF_2CF_2$—, $^3J_{HF}$=12.7 Hz); −121.4 (t, —$CH_2CF_2CF_2$—, $^3J_{HF}$=13.5 Hz); −126.7 (s, —$CH_2CF_2CF_2$—); −126.9 (s, —$CH_2CF_2CF_2$—); −131.9 (d, —$CF_2CF_2H$); −132.0 (d, —$CF_2CF_2H$); −140.1 (t, —$CF_2H$, $^2J_{HF}$=45.2 Hz); −140.1 (t, —$CF_2H$, $^2J_{HF}$=40.1 Hz)

FT-IR υ ($cm^{-1}$):

2105 (N≡C stretch, s); 1718 (C═O stretch, s); 1617, 1543, 1406 (bipyridine ring, m); 1613 (—$COO^-$ stretch, as), 1383 (—COO⁻ stretch, s); 1258, 1230 (—C—O stretch, s); 1169 (CF$_2$ stretch, as); 1126 (CF$_2$ stretch, s)

HR-FAB M⁺:

C$_{36}$H$_{24}$F$_{16}$N$_6$O$_6$RuS$_2$, Calcd m/z 1105.9969, found m/z 1105.9962 (accurate to 3 decimal places)

Identification Data of CT8-TBA

¹H-NMR (500 MHz, CD$_3$OD), δ (ppm):

9.47 (d$_6$, ³J$_{HH}$=5.5 Hz, 1H); 9.42 (d$_6$', ³J$_{HH}$=6.0 Hz, 1H); 8.98 (s, 1H); 8.82 (s, 1H); 8.98 (s, 1H); 8.33 (s, 1H); 8.18 (d, ³J$_{HH}$=5.8 Hz, 1H); 7.79 (d, ³J$_{HH}$=6.0 Hz, 1H); 5.5 Hz, 2H); 7.53 (d, ³J$_{HH}$=6.0 Hz, 1H); 7.65 (d, ³J$_{HH}$=7.52 (d, ³J$_{HH}$=6.0 Hz, 1H); 7.15 (d, ³J$_{HH}$=5.5 Hz, 1H); 6.66 (tt, H$_{10}$''', ²J$_{HF}$=51.5 Hz, J³$_{HF}$=5.5 Hz, 2H); 6.97 (tt, H$_{10}$'', ²J$_{HF}$=51.5 Hz, J³$_{HF}$=5.5 Hz, 2H); 5.07 (s, H$_8$''', 2H); 4.80 (s, H$_8$'', 2H); 4.36 (t, H$_9$''', ³J$_{HF}$=14 Hz, 2H); 9.17 (t, H$_9$'', ³J$_{HF}$=14 Hz, 2H); 1.64 (m, 2H); 1.38 (m, 2H); 0.99 (t, ³J$_{HH}$=7.5, 3H)

¹³C-NMR (113 MHz, CD$_3$OD) δ (ppm):

170.7 (C$_7$); 170.4 (C$_7$'); 160.5 (C$_2$'); 160.0 (C$_2$'); 159.2 (C$_2$''); 158.8 (C$_2$'''); 154.3 (C$_6$); 154.1 (C$_6$'); 152.8 (C$_6$''); 152.7 (C$_6$'''); 149.2 (C$_4$); 148.6 (C$_4$'); 147.5 (C$_4$''); 146.8 (C$_4$'''); 127.0 (C$_3$); 126.2 (C$_3$'); 125.6 (C$_3$''); 125.1 (C$_3$'''); 123.6 (C$_5$); 123.4 (C$_5$'); 121.9 (C$_5$''); 121.8 (C$_5$'''); 134.3 (C$_{14}$ of NCS); 134.2 (C$_{14}$' of NCS); 106-118 (C$_{10}$'''~C$_{13}$''' and C$_{10}$''~C$_{13}$''); 73.2 (C$_8$'''); 72.9 (C$_8$''); 68.9 (C$_9$'''); 68.7 (C$_9$''); 59.5 (—CH$_2$CH$_2$CH$_2$CH$_3$); 24.8 (—CH$_2$CH$_2$CH$_2$CH$_3$); 20.7 (—CH$_2$CH$_2$CH$_2$CH$_3$); 14.0 (—CH$_2$CH$_2$CH$_2$CH$_3$);

¹⁹F-NMR (470.5 MHz, CD$_3$OD), δ (ppm):

−121.3 (t, —CH$_2$CF$_2$CF$_2$—, ³J$_{HF}$=13.1Hz); −121.5 (t, —CH$_2$CF$_2$CF$_2$—, ³J$_{HF}$=10.8 Hz); −126.8 (s, —CH$_2$CF$_2$CF$_2$—); −126.9 (s, —CH$_2$CF$_2$CF$_2$—); −132.0 (d, —CF$_2$CF$_2$H); −132.1 (d, —CF$_2$CF$_2$H); −140.1 (t, —CF$_2$H, ²J$_{HF}$=45.2 Hz); −140.1 (t, —CF$_2$H, ²J$_{HF}$=45.1 Hz)

FT-IR υ (cm⁻¹):

2105 (N≡C stretch, s); 1618, 1543, 1420 (bipyridine ring, m); 1610 (—COO⁻ stretch, as); 1383 (—COO⁻ stretch, s); 1259, 1229 (—C—O stretch, s); 1169 (CF$_2$ stretch, as); 1127 (CF$_2$ stretch, s)

It should be noted that the transition metal complexes of this invention may comprise a fluorinated chain substituted by different numbers of fluorine atoms, such as 4, 7, 8, 12, 13, or 19, and the synthesis method thereof is similar to FIG. 1, except that different fluorinated chains are used in the chelating agent bipyridine ring. Accordingly, if different chelating agents are used, a person skilled in the art can synthesize the transition metal complexes with a different fluorinated chain without undue experimentation. Moreover, the substitution position of the fluorinated chain on the pyridyl ring is not limited to position number 4; a fluorinated chain of other substitution positions can also be synthesized without undue experimentation by using a similar method.

Example 2

Preparation of DSSCs

Figure 2:
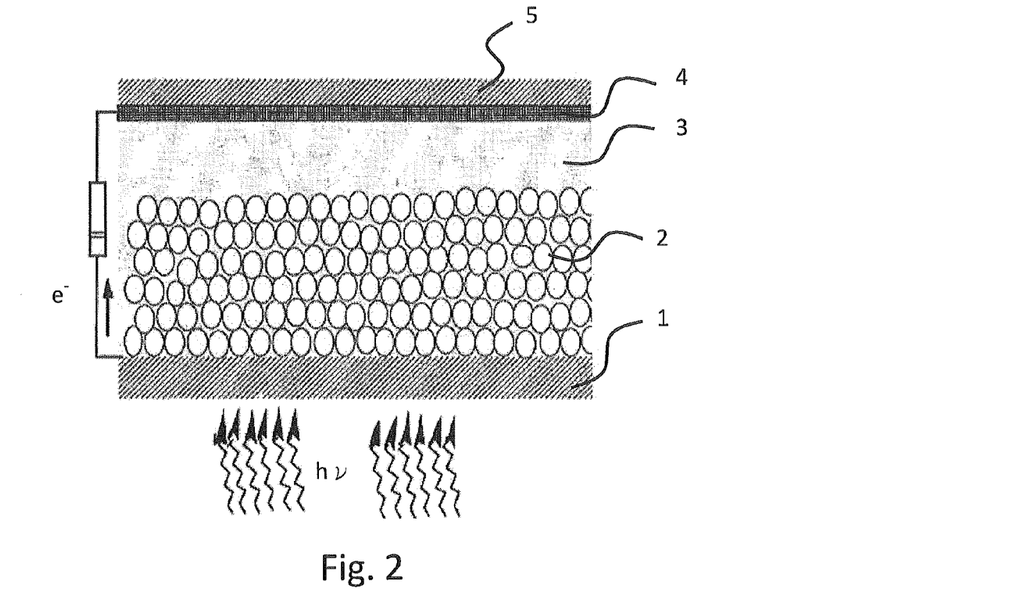
FIG. 2 is an illustrative diagram of a DSSC containing a transition metal complex of this invention.

In order to measure various data of the transition metal complexes of this invention applied to DSSCs, TiO$_2$ thin film electrode with an active area controlled at a dimension of 0.25 cm² with a thickness of 16 μm was provided, heated to 80° C. and dipped into the THF solution containing 3×10⁻⁴ M dye sensitizers for 24 hours. The counter electrode was FTO conductive glass coated with Pt electrode, and the electrolyte was composed of 0.5 M lithium iodide (LiI), 0.05 M iodine (I$_2$), and 0.5 M 4-tert-butylpyridine dissolved in acetonitrile. The electrolyte was injected onto the surface of the counter electrode, and the TiO$_2$ electrode and the counter electrode were tightly sealed to prevent the generation of bubbles. Then a foldback clip was used to fasten the electrodes, such that a DSSC with a sandwich-like structure shown in FIG.2 was obtained, in which conductive glass is represented by numeral 1, dye-containing TiO$_2$ by 2, electrolyte by 3, Pt layer by 4 and the other conductive glass by 5.

Example 3

Measurement of Dye Performance

The performance of the dyes after incorporated into a solar cell is shown below:

(A)

-continued (B)

(C)

(D)

(E)

(F)

Figure 3:
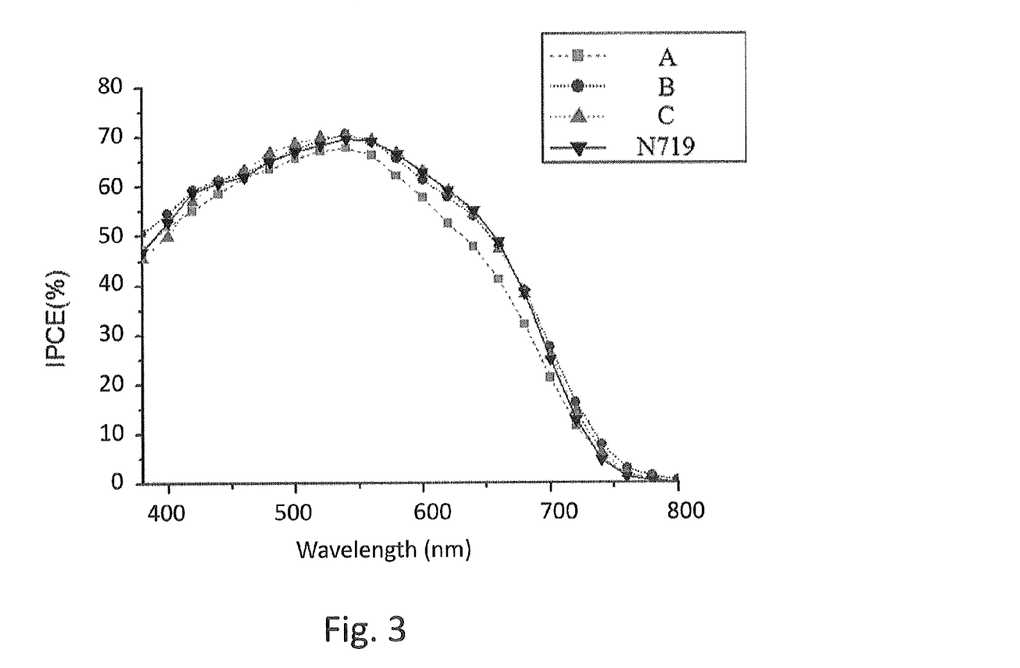
FIG. 3 is the plot of IPCE versus wavelength of a DSSC containing a transition metal complex of this invention.

Dyes A, B and C are incorporated into three solar cells respectively, in which the maximal conversions are obtained when the wavelength of the incident light is at 540 nm. The maximum IPCE measured are A (67.7%), B (70.4%), C (70.2%) and N719 (69.5%). It can be observed that Dye B has the highest conversion efficiency greater than Dye C and Dye A, which has the lowest conversion efficiency. In addition, Dye B has an IPCE greater than that of N719 within wavelength 360 nm~540 nm, and Dye C has an IPCE greater than that of N719 within wavelength 440 nm~600 nm, as shown in FIG. 3. Although Dye A does not have an IPCE greater than N719, its IPCE reaches up to 97.4% of N719. Therefore, the IPCEs of Dyes A, B and C reflect the high performance of the dyes overall.

Detailed photovoltaic parameters under AM1.5 of cells comprising Dyes A, B, C and N719 are shown in Table 1:

TABLE 1

| Dye | $V_{oc}$ (V) | $J_{sc}$ (mA/cm$^{-2}$) | FF | η (%) |
|---|---|---|---|---|
| A | 0.67 | 13.33 | 0.70 | 6.25 |
| B | 0.68 | 15.44 | 0.66 | 6.93 |
| C | 0.68 | 14.98 | 0.67 | 6.82 |
| N719 | 0.71 | 15.37 | 0.67 | 7.31 |
| Z907 | 0.68 | 14.16 | 0.66 | 6.36 | wherein Voc represents Open Circuit Voltage; $J_{SC}$ represents Short Circuit Current; FF represents Fill Factor; η represents the overall efficiency of the cell.

In addition, detailed photovoltaic parameters under AM1.5 of cells comprising Dyes D, E, F and N719 are shown in Table 2:

TABLE 2

| Dye | Voc (V) | Jsc (mA/cm$^2$) | FF | η (%) |
|---|---|---|---|---|
| D | 0.65 | 9.59 | 0.72 | 4.48 |
| E | 0.69 | 13.88 | 0.66 | 6.32 |
| F | 0.66 | 10.94 | 0.72 | 5.11 |
| N719 | 0.72 | 15.24 | 0.64 | 7.02 |

Example 4

Measurement of Dye Performance (II)

Figure 4:
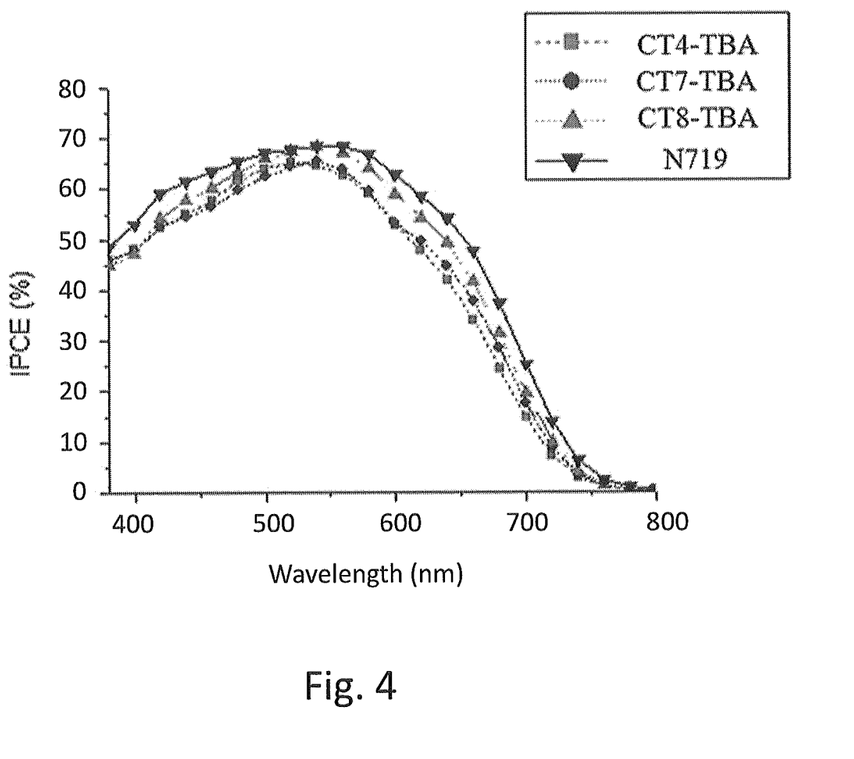
FIG. 4 is the plot of IPCE versus wavelength of a DSSC containing another transition metal complex of this invention.

FIG. 4 is the plot of IPCE versus wavelength of DSSCs containing CT9-TBA, CT7-TBA, and CT8-TBA respectively, and the detailed photovoltaic parameters under AM1.5 of the cells are shown in Table 3:

TABLE 3

| Dye | $V_{oc}$ (V) | $J_{sc}$ (mA/cm$^2$) | FF | $\eta$ (%) |
|---|---|---|---|---|
| CT4-TBA | 0.65 | 13.48 | 0.67 | 5.87 |
| CT7-TBA | 0.71 | 13.80 | 0.66 | 6.46 |
| CT8-TBA | 0.71 | 13.69 | 0.66 | 6.41 |
| N719 | 0.71 | 15.37 | 0.67 | 7.31 |

Example 5

Stability Test of Dyes

I. Dye Adsorption

TiO$_2$ thin film electrodes (14 μm in thickness and 3 cm$^2$ in dimension) coated on FTO conductive glass by the sol-gel process were disposed into a 100° C. oven for 3 hours to remove water. Then 15 mL dyes (including Dye B, Dye C and N719 dissolved in DMF, 2×10$^{-4}$ M) were prepared, and 5 mL of each was used as the reference for spectrum scanning by a UV/Vis spectrophotometer (1 cm path length) to obtain the absorption of the each dye. The exact concentration of each dye before the electrodes were soaked was calculated by using the Beer-Lambert law (formula 1-1) with the molar extinction coefficient of each dye. Moreover, the electrode films coated on the conductive glasses were soaked in the residual 10 mL of each dye, which was used as the working sample, for 12 hours. After adsorption balance was reached, the electrodes were taken from the dyes, and DMF was used to wash the dyes/TiO$_2$ thin films to break the multi-layered bonding of physical adsorption on the thin films. Similarly, the UV/Vis spectrophotometer was used to measure the adsorption of the working samples, and the Beer-Lambert law was used to calculate the exact concentration of each dye after the electrodes were soaked. The amounts of dyes adsorbed by the electrode thin films were obtained by subtracting the number of mole of each dye after the electrodes were soaked from the number of mole of each dye before the electrode was soaked. Then the dyes/electrode thin films coated on the conductive glasses were scraped off to measure their weights, and the adsorption amount of each dye on the respective TiO$_2$ thin film electrode were calculated by formula 1-2:

$$A = \epsilon BC \quad (1\text{-}1)$$

wherein A: absorption; ε: molar extinction coefficient; B: path length; C: concentration of sample $$\text{Dye adsorption amount} = [\text{amount of dye adsorbed by TiO}_2 \text{ electrode/total amount of adsorbed dye and TiO}_2 \text{ electrode}] \times 2.4 \quad (1\text{-}2)$$

The adsorption result is shown below:

TABLE 4

| | Dye | | |
|---|---|---|---|
| | B | C | N719 |
| Amount of dye before TiO$_2$ electrode was soaked (×10$^{-6}$ mol) | 3 | 3 | 3 |
| Amount of dye after TiO$_2$ electrode was soaked (×10$^{-6}$ mol) | 2.622 | 2.623 | 2.740 |
| Amount of dye adsorbed by TiO$_2$ electrode (×10$^{-6}$ mol) | 0.378 | 0.377 | 0.26 |
| Total amount of adsorbed dye and TiO$_2$ electrode (mg) | 3.6 | 3.7 | 3.3 |

TABLE 4-continued

| | Dye | | |
|---|---|---|---|
| | B | C | N719 |
| Dye adsorption calculated by formula 1-2 (×10$^{-7}$ mol/cm$^2$) | 2.52 | 2.45 | 1.89 |

From Table 4, it can be observed that, compared with N719, which is widely known for its high performance, Dye B and Dye C have a greater adsorption amount; thus, the dyes of this invention can provide an enhanced performance.

II. Dye Desorption

Dyes/TiO$_2$ electrode thin films (including 3×10$^{-4}$ M Dye B, Dye C, and N719; the electrode thin films have a dimension of 0.25 cm$^2$ with a thickness of 16 μm) soaked in THF for 12 hours to reach adsorption balance were treated by alkali (5M NaOH solution) to completely wash off the dye adsorbed on the surface of the thin film. The desorption result is as follows:

| | Dye | | | |
|---|---|---|---|---|
| | B | C | N719 | Z907 |
| Desorption? | No | No | Yes | Yes |

As shown above, Dye B and Dye C both demonstrate long-term stability better than N719 and have stronger resistance to strong alkali, so they do not fall off easily after being used for a period of time. Particularly, even when compared with Z907, which is widely known for its long-term stability, the dyes of this invention demonstrates stability better than Z907. Therefore, solar cells using the dyes of this invention have a longer service life.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A method of preparing photovoltaic cells, comprising:
   providing a transition metal complex; and
   preparing photovoltaic cells containing the transition metal complex;
   wherein the transition metal complex has the following chemical structure:

wherein $FC_1$ and $FC_2$ are each independently —$CH_2$—O—$CH_2$—$R_f$, and $R_f$ is an alkyl chain substituted by 1 to 30 fluorine atoms, and wherein Me is at least one iron, ruthenium, and osmium.

* * * * *